United States Patent [19]
Gianino

[11] Patent Number: 5,736,101
[45] Date of Patent: Apr. 7, 1998

[54] AUTOMATED ANALYTICAL INSTRUMENT HAVING A FLUID SAMPLE HOLDING TRAY TRANSPORT ASSEMBLY

[75] Inventor: F. Thomas Gianino, Methuen, Mass.

[73] Assignee: Rehring Diagnostics, Westwood, Mass.

[21] Appl. No.: 464,009

[22] Filed: Jun. 5, 1995

Related U.S. Application Data

[62] Division of Ser. No. 180,760, Jan. 10, 1994, abandoned, which is a continuation of Ser. No. 907,703, Jul. 1, 1992, abandoned.

[51] Int. Cl.$^6$ ............................................. G01N 35/02
[52] U.S. Cl. .......................... 422/65; 422/63; 436/47; 436/48
[58] Field of Search ..................... 422/63–65, 100; 436/43, 47, 48, 49, 174, 180

[56] References Cited

U.S. PATENT DOCUMENTS

| | | | |
|---|---|---|---|
| 3,533,744 | 10/1970 | Unger | 23/230 |
| 3,897,216 | 7/1975 | Jones | 422/65 |
| 3,917,455 | 11/1975 | Bak et al. | 455/65 |
| 4,168,955 | 9/1979 | Allington | 422/65 |
| 4,609,017 | 9/1986 | Coulter et al. | 141/1 |
| 4,678,752 | 7/1987 | Thorne et al. | 435/291 |
| 4,731,225 | 3/1988 | Wakatake | 422/65 |
| 4,982,553 | 1/1991 | Itoh | 53/246 |
| 5,008,082 | 4/1991 | Shaw | 422/65 |
| 5,055,408 | 10/1991 | Higo et al. | 436/48 |
| 5,158,895 | 10/1992 | Ashihara et al. | 436/526 |
| 5,176,880 | 1/1993 | Iwasaki et al. | 422/63 |
| 5,209,903 | 5/1993 | Kanamori et al. | 422/65 |
| 5,380,488 | 1/1995 | Wakatake | 422/65 |
| 5,518,688 | 5/1996 | Gianino | 422/65 |

Primary Examiner—Long V. Le
Attorney, Agent, or Firm—Frommer Lawrence & Haug LLP

[57] ABSTRACT

An automated analytical instrument for conducting assays for components of interest in fluid samples. The instrument includes a testing system for assaying a fluid sample for a component of interest, a fluid dispensing assembly, an assembly for providing an assay module to the testing system and a fluid sample holding tray transport assembly for transporting a fluid sample holding tray carrying fluid sample holding containers to the fluid dispensing assembly and away from the fluid dispensing assembly. The transport assembly includes a conveyor, a fluid sample holding tray loading unit and a fluid sample holding tray unloading unit. The conveyor includes a carriage which is slidably mounted on a rail and moved along the rail by an endless belt which is fixedly attached to the carriage and driven by a reversible motor. In the operation of the instrument, one or more fluid sample holding trays are placed onto the fluid sample holding tray loading unit. Each fluid sample holding tray so loaded on to the fluid sample tray loading unit is then automatically transferred one at a time onto the carriage, moved by the carriage to the fluid dispensing assembly where fluid samples are aspirated therefrom and then moved to the fluid sample holding tray unloading unit where it is automatically unloaded.

1 Claim, 19 Drawing Sheets

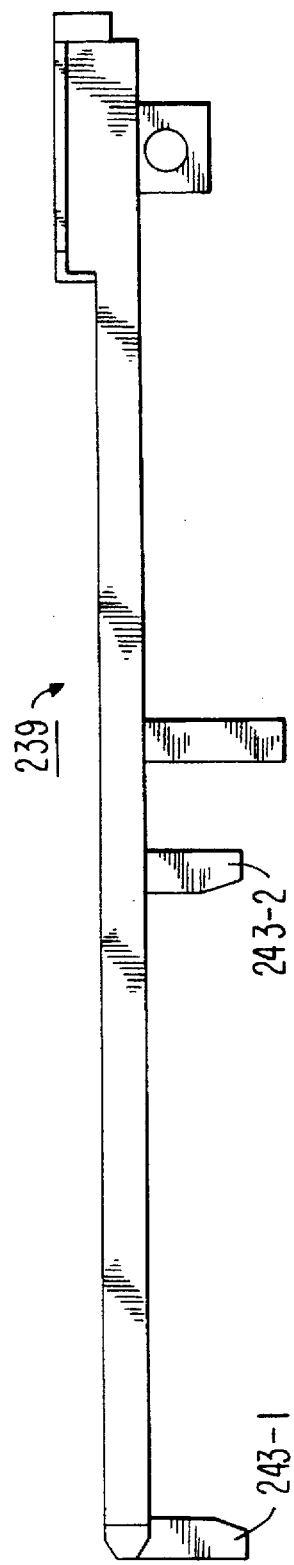

AUTOMATED ANALYTICAL INSTRUMENT HAVING A FLUID SAMPLE HOLDING TRAY TRANSPORT ASSEMBLY

This application is a division of application Ser. No. 08/180,760, filed Jan. 10, 1994, now abandoned, which is a continuation of application Ser. No. 07/907,703, filed Jul. 1, 1992, now abandoned.

BACKGROUND OF THE INVENTION

The present invention relates generally to automated analytical instruments and more particularly to automated analytical instruments for conducting assays for components of interest in fluid samples.

In recent years, a number of automated instruments have been developed to perform analyses of fluid samples. As is known in the art, such instruments may be used to test various types of biological fluids for substances of interest, for example, to find evidence of disease, to monitor therapeutic drug levels, and the like. Typically, such automated analytic instruments utilize either liquid reagents or dry reagents to assay for a substance of interest. Various different types of assay devices are known for use in such automated instruments including, for example, dry thin-film multilayer assay elements which are typically mounted in an assay module and capillary assay devices.

Generally speaking, automated analytical instruments for conducting assays for substances of interest in fluid samples typically include a plurality of containers for holding the fluid samples to be tested and may include containers for holding the desired reagents. The instruments also typically include one or more fluid dispensing units for metering out quantities of the fluid samples to be analyzed, a temperature controlled chamber wherein the assay devices are allowed to incubate for an appropriate period of time, an analyzing system for measuring some property related to the substance of interest in the fluid samples being tested and some mechanism for bringing the sample holding containers to a location where they can be accessed by a fluid dispensing unit.

In copending, commonly assigned U.S. patent application Ser. No. 732,053 filed on Jul. 18, 1991 in the name of Robert C. MacIndoe, Jr., now abandoned, there is disclosed an automated analytical instrument of the type which uses assay modules to perform assays for components of interest in fluid samples. The instrument includes a supply apparatus for holding a supply of assay modules, a testing system which includes apparatus for testing the fluid samples using the assay modules, a fluid sample cup holder having a plurality of fluid sample holding cups, a pair of fluid sample dispensing units and an assay module transfer apparatus for transferring an assay module to be used from the supply apparatus to the testing system. The assay module transfer apparatus includes an assay module transfer unit which is mounted on a supporting structure and is movable vertically. The assay module transfer unit includes a mechanism for pulling the assay module out of the assay module supply apparatus and a mechanism for pushing the assay module so obtained into the testing system. By moving the assay module transfer unit vertically, the assay module transfer unit can be aligned with assay modules disposed at different levels in the supply apparatus. In the operation of the instrument, the fluid sample cup holder travels back and forth between fluid dispensing units wherein quantities of fluid samples are dispensed into the assay modules being used for testing the fluid samples.

In U.S. Pat. No. 4,152,390, there is described an automated chemical analytical instrument which included, in addition to a testing system wherein the testing takes place, a supply unit for holding a plurality of assay modules and a transfer apparatus for transferring an assay module from the supply unit to the testing system. The assay modules are stacked in containers, which may be received in a nest of the analyzing apparatus with a spring biased plunger arranged to enter the container through an opening. The plunger engages a movable element located in the container behind the stack of modules to urge the top module forwardly toward the testing system portion of the instrument. The instrument also includes a sample tray which is removably mounted on a pair of tracks. A plurality of cups containing the biological fluids to be tested are placed, presumably by the operator, onto the sample tray.

As can readily be appreciated, the need exists for an automated analytical instrument for conducting assays of fluid samples which includes a more automated arrangement for transporting the containers having the fluid samples to be tested to the fluid dispensing unit (or units) and then moving the containers out of the way after quantities of the fluid samples to be tested have been withdrawn.

SUMMARY OF THE INVENTION

It is an object of the present invention to provide a new and improved automated analytical instrument.

It is another object of this invention to provide an automated analytical instrument for conducting assays of fluid samples which includes a new and novel arrangement for holding fluid samples and for transporting fluid samples so held to a fluid sample dispensing unit.

Additional objects, as well as features and advantages, of the present invention will be set forth in part in the description which follows, and in part will be obvious from the description or may be learned by practice of the invention. The objects, features and advantages of the present invention may be realized and attained by means of the instrumentalities and combinations particularly pointed out in the appended claims.

Accordingly, to achieve the foregoing objects and in accordance with the purpose of the present invention as broadly set forth and embodied herein, an automated analytical instrument for use in conducting assays for a component of interest in fluid sample is provided. The instrument includes a fluid sample holding tray for holding a plurality of containers having fluid samples therein, a testing system for assaying a fluid sample for a component of interest, a fluid sample dispensing unit for dispensing a quantity of a fluid sample from a container in said fluid sample holding tray to an assay device utilized in the testing system for analytical purposes and a fluid sample holding tray transport assembly for transporting said fluid sample holding tray to said fluid sample dispensing unit and away from said fluid sample dispensing unit after quantities of the fluid samples in said fluid sample holding tray have been withdrawn for testing. The fluid sample holding tray transport assembly includes a conveyor for moving the fluid sample holding tray along a path past said fluid sample dispensing unit, a loading unit for automatically loading said fluid sample holding tray onto said conveyor and an unloading unit for automatically unloading said fluid sample holding tray from said conveyor.

BRIEF DESCRIPTION OF THE DRAWINGS

The accompanying drawings, which are hereby incorporated into and constitute a part of this specification, illustrate the preferred embodiments of the invention and, together with the description, serve to explain the principles of the invention. In these drawing wherein like reference numerals represent like parts:

FIG. 21 is a front view of the loader arm shown in FIG. 20.

DETAILED DESCRIPTION OF THE PREFERRED EMBODIMENTS

Figure 1:
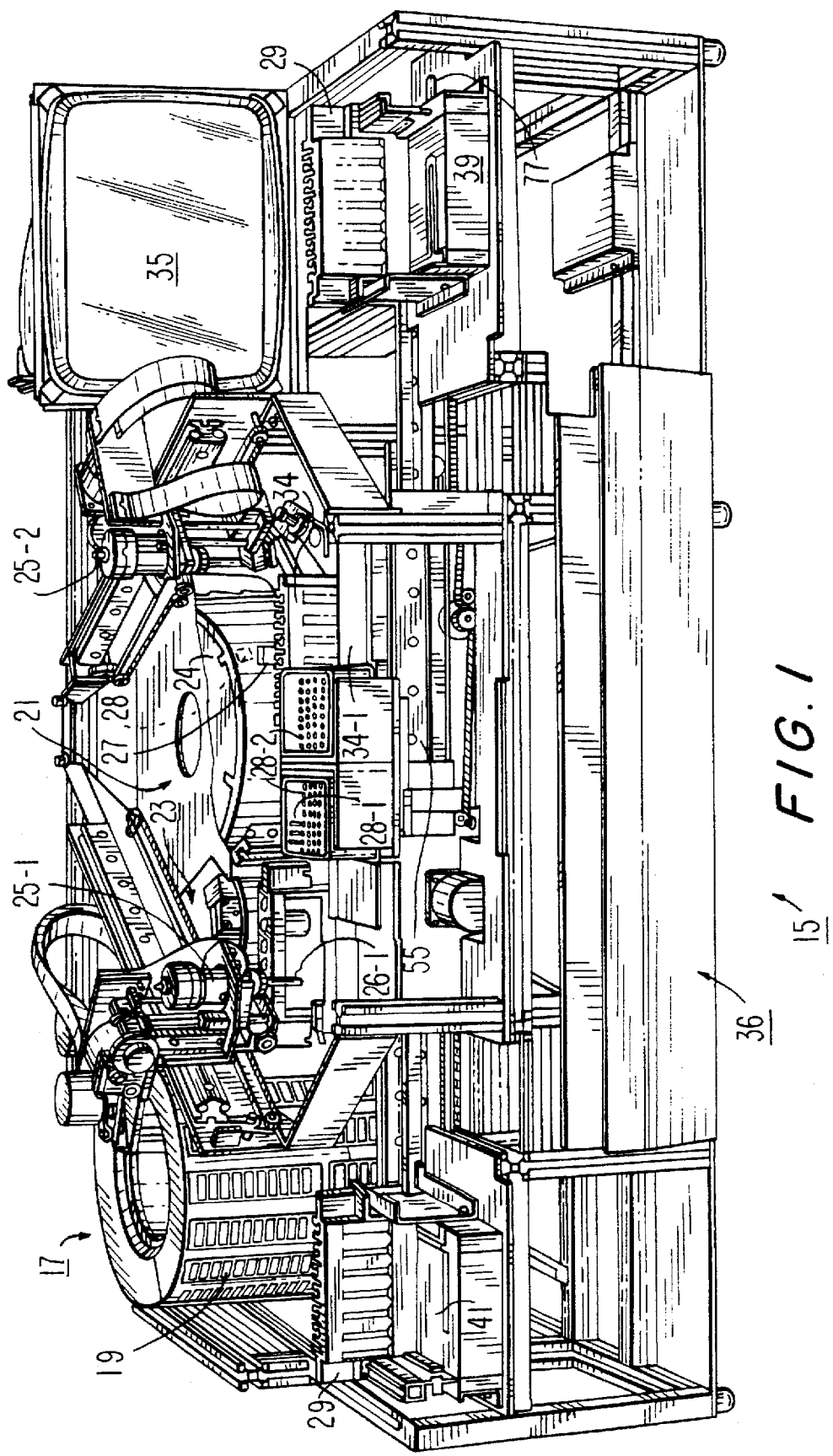
FIG. 1 is a simplified perspective view of an automated analytical instrument constructed according to this invention.

Referring now to FIG. 1, there is shown an automated analytical instrument constructed according to the teachings of the present invention for conducting assays for components of interest in fluid samples, the instrument being identified by reference numeral 15. Portions of instrument 15 not pertinent to this invention are neither shown nor discussed.

Instrument 15 includes an assay module supply apparatus 17 for storing a plurality of unused assay modules 19, each containing one or more reagents useful in the detection of a particular component in a fluid sample. Instrument 15 also includes a temperature controlled chamber 21 wherein the testing of fluid samples occurs in the manner hereinafter described and an assay module transport assembly 23 for transporting assay module, one at a time, from supply apparatus onto a rotatably mounted turntable 24 disposed within chamber 21. Instrument 15 further includes a pair of pipette assemblies 25-1 and 25-2 for dispensing quantities of fluid samples to assay modules disposed at a pair of metering stations 26 and 28 (shown schematically) located within chamber 21. In the preferred embodiment illustrated in FIG. 1 the metering stations are located in proximity to turntable 24 and the assay modules are removed form the turntable and deposited at a metering station. Subsequent to receiving the fluid samples the assay modules are returned to the turntable where they reside during the incubation period. It will be appreciated by those skilled in the art that the sample fluid may be deposited on the assay modules prior to their insertion in the temperature controlled chamber 21 or when the assay modules are located on the turntable.

The instrument 15 additionally may include a plurality of preferably three, optical read stations (not shown) located within chamber 21 for measuring a signal generated in the assay module which is a function of the concentration of a component of interest in the sample fluid. The optical read stations as is the case with the metering stations 26 and 28, are located in proximity to the turntable 24. Automated shuttle mechanisms (not shown) are used to transport assay modules back and forth between turntable 24 and metering stations 26 and 28 and back and forth between turntable 24 and an optical read station. Each of the optical read stations has associated with it an optical read device, one of which is shown at 27 for purposes of illustration. In the preferred embodiment illustrated in FIG. 1 the optical read devices are located outside the temperature controlled chamber 21 and read the signals generated in the assay modules through an opening in the bottom wall of the chamber 21. Pipette assemblies 25 obtain pipette tips 28-1 from a pipette tip holding container 28-2 suitably located withn instrument 15.

Figure 2:
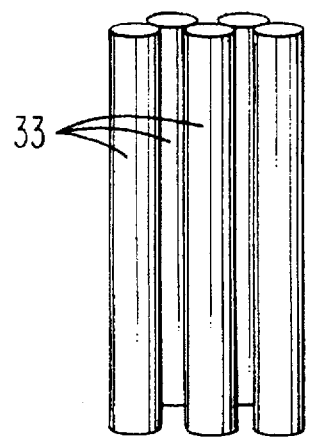
FIG. 2 is a perspective view of a plurality of the containers for holding fluid samples for use with the automated analytical instrument shown in FIG. 1.

Instrument 15 also includes a fluid sample holding tray transport assembly 31 (FIG. 3) which serves to transport fluid sample holding trays 29 within instrument 15 as will hereinafter be discussed. Each fluid sample holding tray 29 is adapted to hold a plurality of sample fluid containers 33. A plurality of sample fluid containers 33 are shown in FIG. 2. Containers 33 can be either cups or tubes. For illustrative purposes only, container 33 are shown as being tubes.

Instrument 15 additionally can include a diluent tray 34 for holding diluents and a diluent tray transport assembly 34-1. Transport assembly 34-1 serves to transport diluent tray 34 to a desired location within instrument 15. Transport assembly 34-1 includes a rail on which tray 34 is mounted and a motor driven chain attached to tray 34 for moving tray 34 on the rail.

Instrument 15 further includes a microprocessor (not shown) for controlling the operation of the various components within instrument 15. It should be noted that when reference is made herein to a microprocessor it is intended to include the overall controlling processing unit (CPU) as well as any number of embedded single chip controllers each of which is typically utilized to control the operation of one mechanism such as a stepper motor for driving various assemblies as will be described herein. Instrument 15 also preferably includes a CRT screen 35 which can be used to provide a visual display of the assay results obtained from the analyses performed by the instrument. In a preferred embodiment, screen 35 is a touch screen which allows an operator to input information and instructions to the instrument 15. All of the components noted above are supported in a frame 36.

Figure 3:
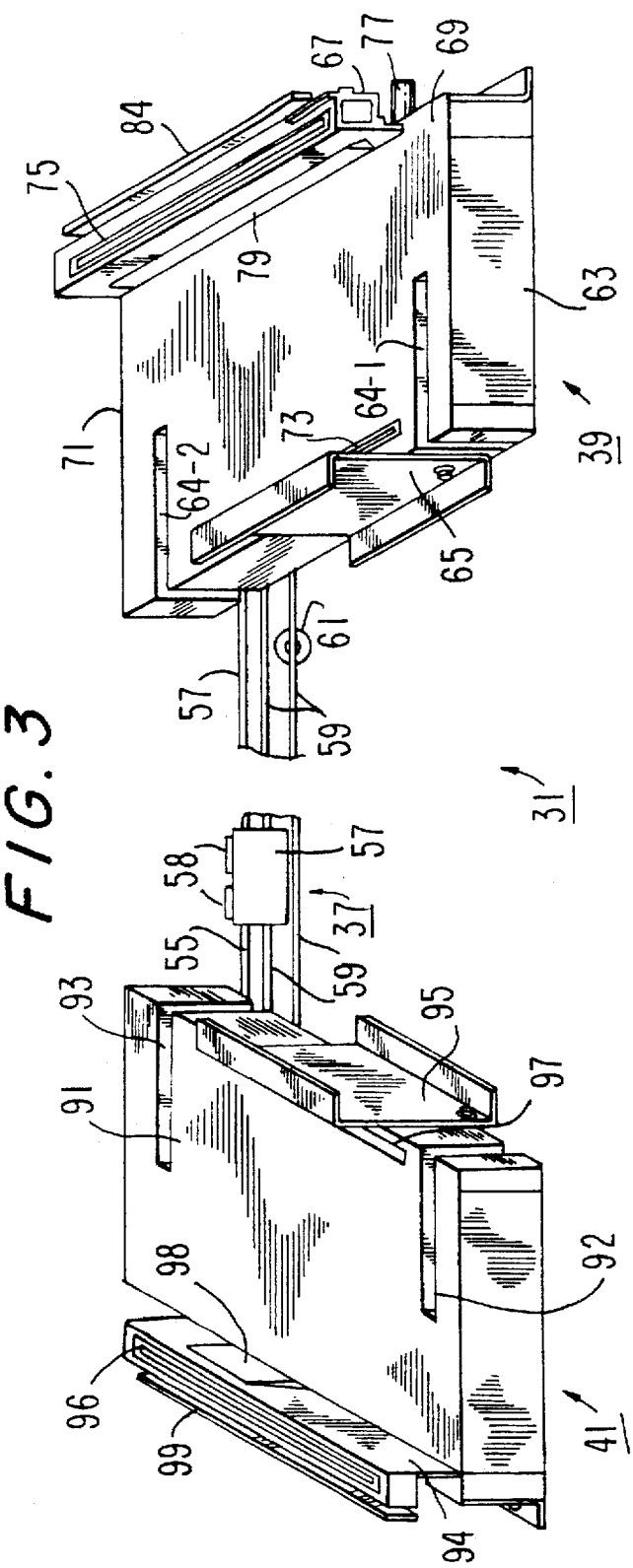
FIG. 3 is a simplified perspective view taken from the front right of the fluid sample holding tray transport assembly shown in FIG. 1.

Fluid sample holding tray transport assembly 31, which is shown separately in FIG. 3, includes a conveyor 37 for moving fluid sample holding trays 29 along a path past pipette assemblies 25, a sample holding tray loading unit 39 for automatically loading fluid sample holding trays 29 onto conveyor 37 and a sample holding tray unloading unit 41 for automatically unloading fluid sample holding trays from conveyor 37.

In FIG. 1, tow fluid sample holding trays 29 are shown, one at sample tray loading unit 39 and the other at sample tray unloading unit 41; however, it should be understood that the number of fluid sample holding trays 29 shown in FIG. 1 and their locations within instrument 15 are for illustrative purposes only.

In the operation of instrument 15, fluid samples to be tested are poured into fluid sample containers 33. Containers 33 are then loaded into trays 29, Alternately, containers 33 could be filled after they are loaded into trays 29. One or more trays 29 are then placed by the operator on loading unit 39, the number of trays 29 placed thereon depending on the number of fluid samples to be tested and the number of trays 29 that can actually fit on loading unit 39. At the same time, each pipette assembly 25 takes a tip 25-1 from holding container 28-2. Trays 29 are placed on loading unit 39 in a row, one behind the other. In loading unit 39, the first tray 29 in the row is automatically advanced to the tray loading area at the rear of loading unit 39, loaded onto conveyor 37 and then moved by conveyor 37 to a predetermined one of the pipette assemblies 25. After quantities of the desired fluid samples have been aspirated from tray 29 by a pipette assembly 25, tray 29 is moved along conveyor 37 to unloading unit 41 where it is unloaded form conveyor 37. The next tray 29 in the row is then loaded from loading unit 39 to conveyor 37 and so forth. The loading, moving, dispensing and unloading operations are all controlled by the microprocessor.

Figure 4:
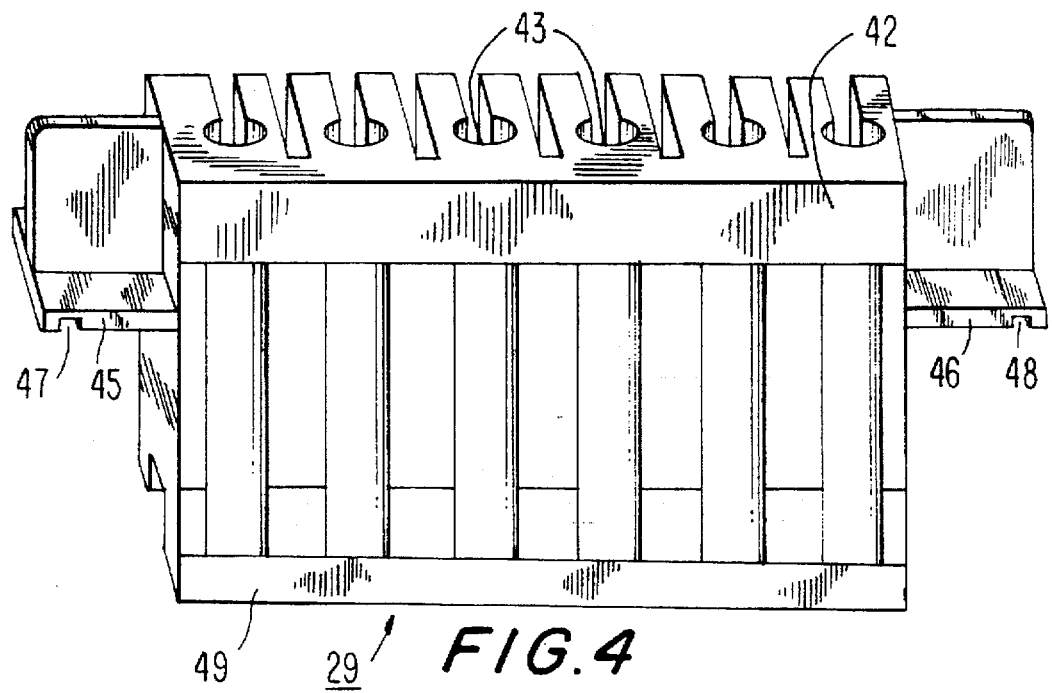
FIG. 4 is a perspective view taken from the top of one of the fluid sample holding trays shown in FIG. 1.
Figure 5:
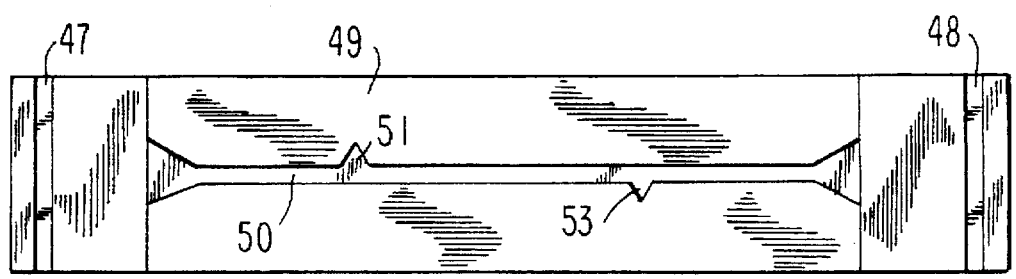
FIG. 5 is a bottom view of the fluid sample holding tray shown in FIG. 1.

A perspective view taken from the top of a fluid sample holding tray 29 is shown in FIG. 4 and a bottom view of the fluid sample holding tray 29 is shown in FIG. 5. Tray 29 as illustrated, can be a molded polymeric structure which is shaped to include a top portion 42 having a plurality of openings 43 in which can be removably mounted containers 33, left and right side flanges 45 and 46, respectively, having slots 47 and 48 respectively and a bottom wall 49 which includes a longitudinal slot 50 having a pair of integrally formed notches 51 and 53. Openings 43 are shaped and sized according to the shape of containers 31 being used (i.e. cups or tubes).

Conveyor 37 includes a monorail 55 which extends from loading unit 39 to unloading unit 41 along a path which passes by pipette assemblies 25-1 and 25-2. A carriage 57 adapted to support a fluid sample holding tray 29 is slidably mounted on monorail 55. Carriage 57 includes a pair of spring loaded detents 58 which are used to removably secure carriage 57 to a tray 29 to be transported by carriage 57. Carriage 57 is fixedly secured to a rotatably mounted endless belt 59. Belt 59 is driven by a reversible stepper motor 61, the operation of which is controlled by the microprocessor. When motor 61 is energized, endless belt 59 will move causing carriage 57 to slidably move along monorail 55, the direction of movement of carriage 57 on monorail 55 depending on the rotation of the drive shaft on motor 61.

Figure 6:
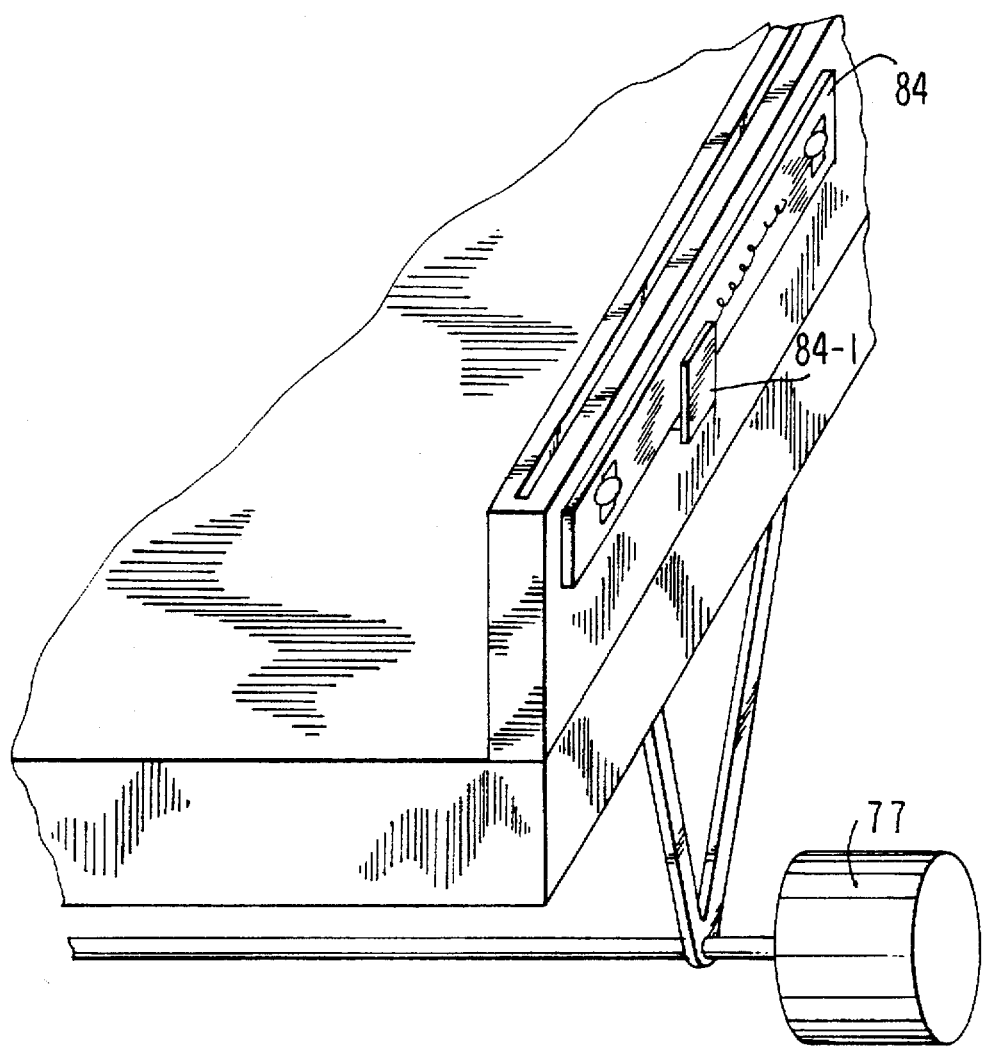
FIG. 6 is a fragmentary perspective view taken from the right of the sample tray loading unit shown in FIG. 2.
Figure 6A:
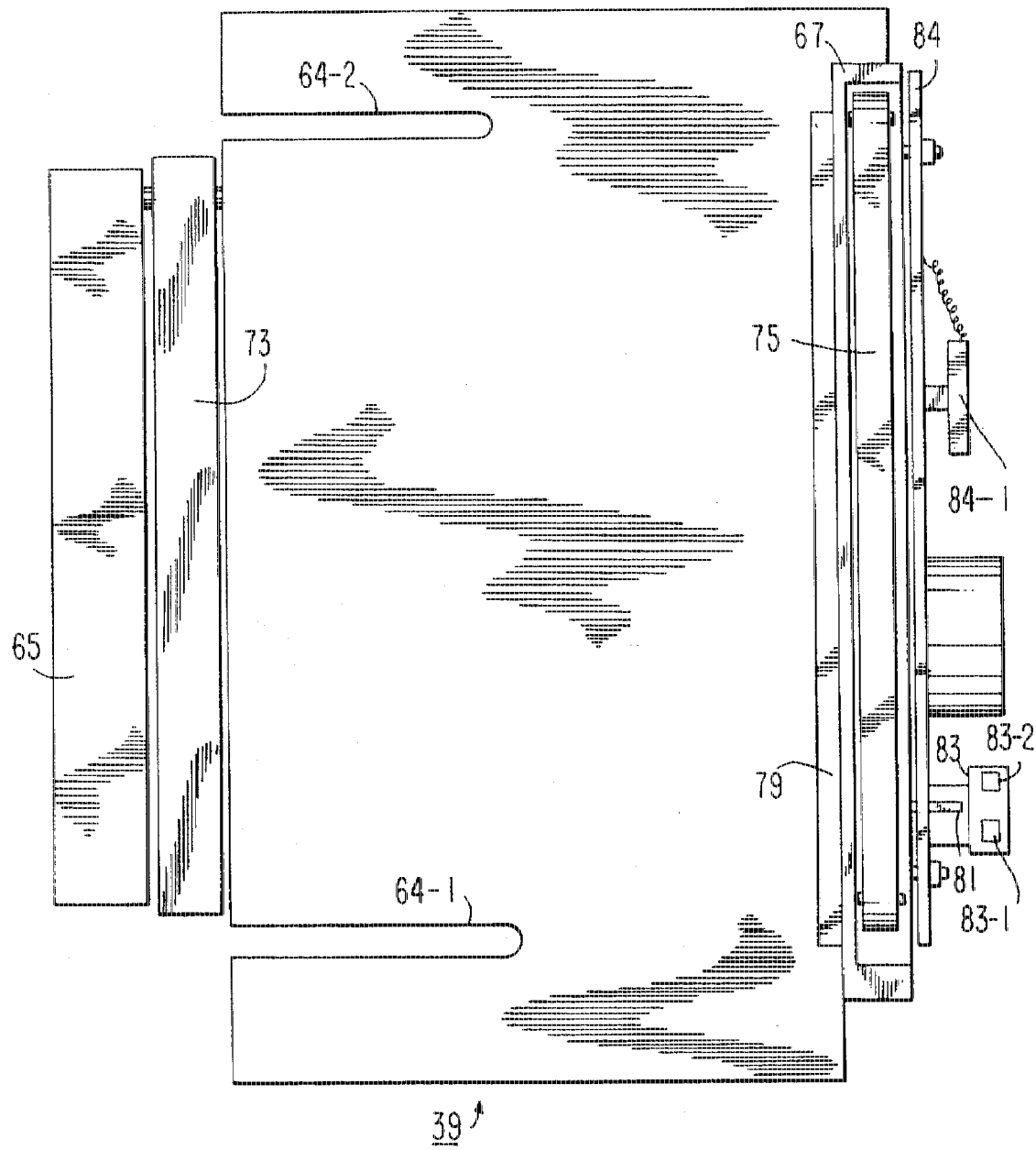
FIG. 6(a) is a top view of the loading tray shown in FIG. 6.
Figure 7:
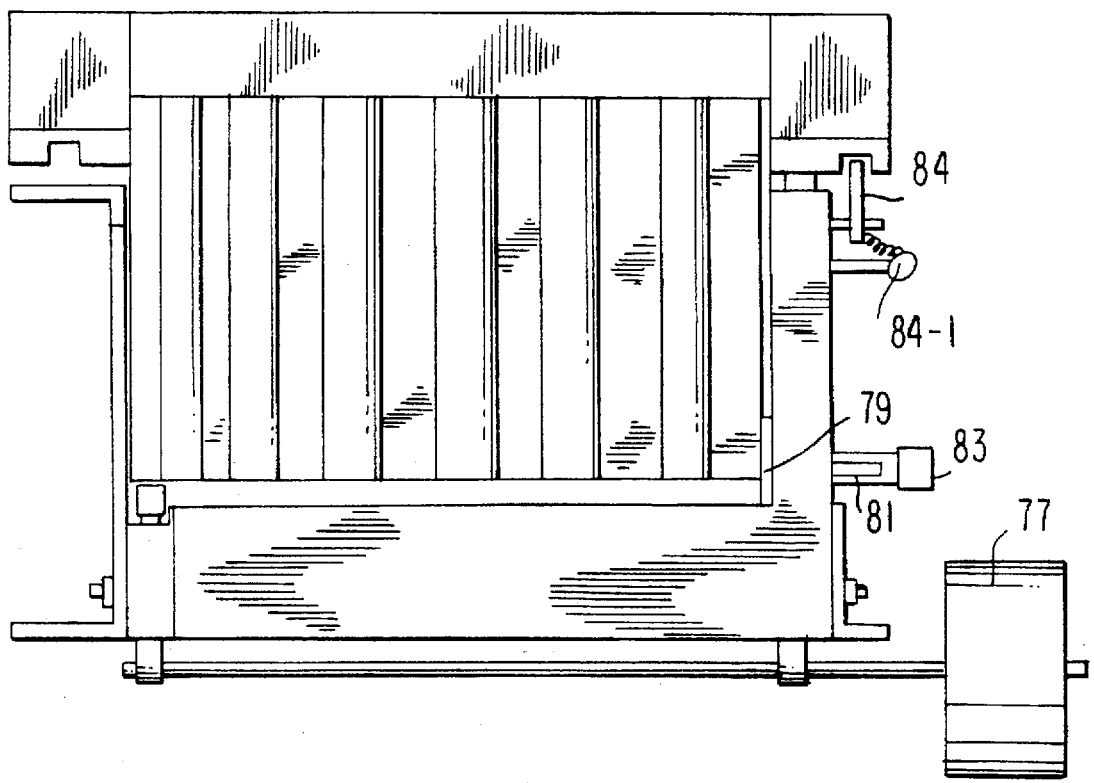
FIG. 7 is a front view showing a fluid sample holding tray seated on the tray loading unit in FIG. 1.

Loading unit 39, see especially FIGS. 6 and 6(a), is an elongated rigid structure and includes a base 63 having front and rear lateral slots 64-1 and 64-2, respectively, a pair of side walls 65 and 67 which extend upwardly on either side of base 63, a front area 69 and a rear area 71. Loading unit 39 is positioned with respect to conveyor 37 so that rear slot 64-2 is aligned with monorail 55. A pair of endless belts 73 and 75 are rotatably mounted on loading unit 39, one on each side thereof, and extend from the front area 69 of unit 39 to the rear area 71 of unit 39. Endless belts 73 and 75 are driven by a motor 77 which is coupled to both belts. Belt 73 is disposed lower than belt 75 so as not to interfere with the loading of a tray 29 onto carriage 57 as will hereinafter be explained. When a tray 29 is placed on loading unit 39, bottom wall 49 will be seated on belt 73 and side flange 46 will be seated on belt 75. Motor 77 is controlled by the microprocessor. Belts 73 and 75 are used to carry tray 29 to rear area 71 of unit 39 where it is automatically transferred to carriage 57. An elongated detector plate 29 extending from the front area 69 of unit 39 to the rear area 71 of unit 39 is pivotally mounted on the inside surface of outer side wall 67. A signal interrupter plate 81 is fixedly attached to detector plate 79. A first sensor unit 83 is mounted on tray 29 in close proximity to plate 81.

For purposes of illustration sensor unit 83 is shown being mounted on the front area 69 of loading unit 39. It will be appreciated that the sensor unit 83 can be mounted at any suitable location along the side of loading unit 39. First sensor unit 83 includes an LED 83-1 and a light detector 83-2. When there is not tray 29 in loading unit 39, plate 79 is pivoted outward at an angle of about 30 degrees, and detector 83-2 receives a light signal from LED 83-1 and sends an electrical signal to the microprocessor indicating that the light signal is received. When a tray 29 is placed in loading unit 39 at any location along base 63, plate will be pivoted in causing plate 81 to interrupt the signal sent by first sensor unit 83 to the microprocessor. This in turn will cause the microprocessor to activate motor 77.

Unit 39 also includes a 45 degree movable plate 84 which is mounted on the outside of side wall 67. Movable plate 84 is normally in a raised position. Movement of plate 84 is controlled by a solenoid 84-1. Plate 84 serves two purposes, namely, to guide tray 29 as it is moved back in loading unit 39 to rear area 71 and to prevent tray 29 from moving out on monorail 55 until allowed to do so by the microprocessor. When a tray 29 is placed on loading unit 39, plate 84 will extend up in slot 48 of tray 29. Plate 84 can also be utilized to serve a latching function, e.g., to restrain tray 29 and prevent it from being moved accidentally on the loading unit 39.

Figure 8:
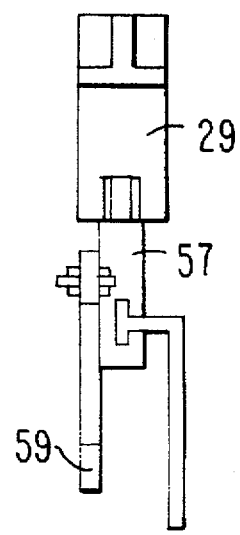
FIG. 8 is an end view showing the carriage in the transport assembly in FIG. 3 in engagement with a fluid sample holding tray in FIG. 4.

When tray 29 has been moved to the rear area of loading unit 39 and is in position to receive and engage carriage 57 (i.e. bottom slot 50 on tray 29 is aligned with rear slot 64-2 on the loading unit), a signal is sent by a second sensor 85 (not shown) which is identical to sensor 83 to the microprocessor. This signal causes the microprocessor to send out a signal which stops motor 77, which drives belts 73 and 75, and a signal which starts motor 61, which moves carriage 57 on monorail 55 so that it can slide into slot 50 in tray 29. As carriage 57 moves under tray 29, spring detents 58 on the top of carriage 57 engage the notches 51 and 53 in tray 29, thereby releasably securing carriage 57 to tray 29. An end view showing carriage 57 in engagement with tray 29 is shown in FIG. 8. As soon as carriage 57 engages tray 29, a signal is sent to the microprocessor by a third sensor 87 (not shown) which is also identical to sensor 83. The signal from the third sensor 87 to the microprocessor causes it to send out a signal changing the direction of rotation of motor 61 which moves belt 59. At the same time, the microprocessor sends out a signal to solenoid 84-1 which causes plate 84 to be lowered. These two signals from the microprocessor will enable carriage 57 to move back out on monorail 55 carrying with it a tray 29. Carriage 57 will stop at a pipette assembly 25-1 or 25-2, the particular pipette assembly being controlled by the microprocessor. After the desired fluid samples have been withdrawn form tray 29 for analysis, carriage 57 will transport tray 29 to unloading unit 41.

Unloading unit 41 is similar in construction to loading unit 39 in that it includes a base 91 having front and rear slots 92 and 93, side walls 94 and 95, a pair of belts 96 and 97 driven by a motor (not shown), a detector plate 98 coupled to an interrupter plate (not shown) which is similar to interrupter plate 81 of loading unit 39 (FIG. 6A), a 45 degree movable latch plate 99 and a set of three sensors (not shown). However, detector plate 98 only extends forward a short distance from the rear of the unit. Latch plate 99 is in a normally raised position as is the case with movable plate 84. In order to allow tray 29 to be moved onto unload station 41, latch plate 99 must be lowered. A microprocessor-controlled solenoid (not shown) causes latch plate 99 to be lowered. In the operation of unit 41, as soon as a tray 29 has been brought in, latch plate 99 will be raised, carriage 57 will move back out leaving tray 29 on unit 41 and belts 96 and 97 will move tray 29 forward. As soon as tray 29 moves past plate 98, motor 97-1 will be stopped causing belts 96 and 97 to stop movement.

Figure 9:
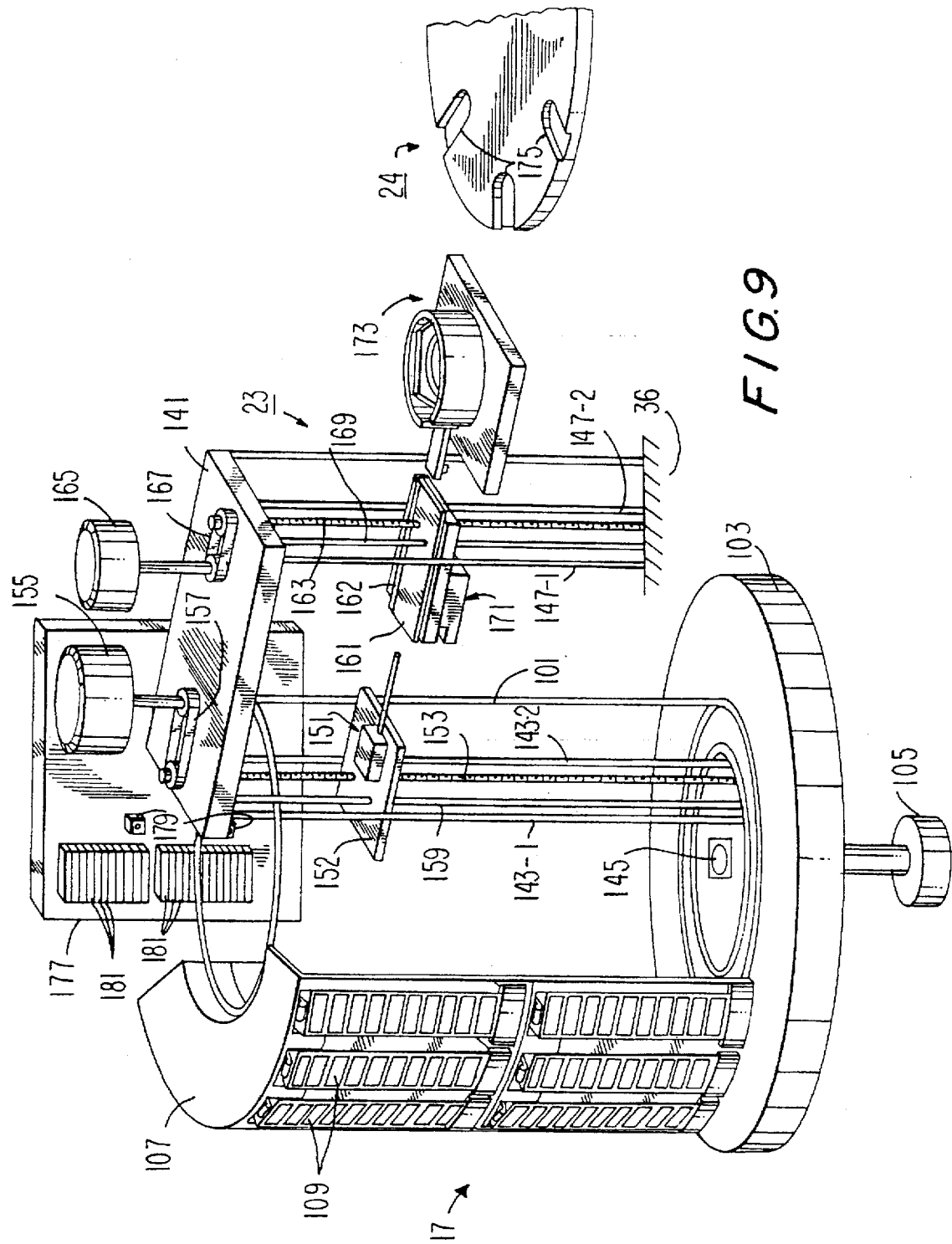
FIG. 9 is a simplified perspective view of those components of the automated analytical instrument of FIG. 1 that pertain to the assay module transport assembly certain elements of the assay module transport assembly being shown in block form for simplicity and clarity.

Referring now to FIG. 9, assay module supply apparatus 17, assay module transport assembly 23, and a portion of turntable 24 of chamber 21 are shown and hereinafter described in detail to illustrate the operation of assay module transport assembly 23.

As can be seen, supply apparatus 17 comprises a cylindrically shaped frame 101, a rotatably mounted, annularly-shaped turntable 103 upon which frame 101 is supported, a stepper motor 105 which is coupled to turntable 103 through a belt (not shown) for rotating turntable 103, a plurality of arcuately-shaped assay module supply units or segments 107 (only one of which is shown in FIG. 9 for clarity) which are removably mounted on the outside of frame 101, and a plurality of magazines 109 which are removably mounted in each segment 107. The operation and direction of motor 105 and, hence, the rotational position of segments 107 are controlled by the microprocessor.

Figure 10:
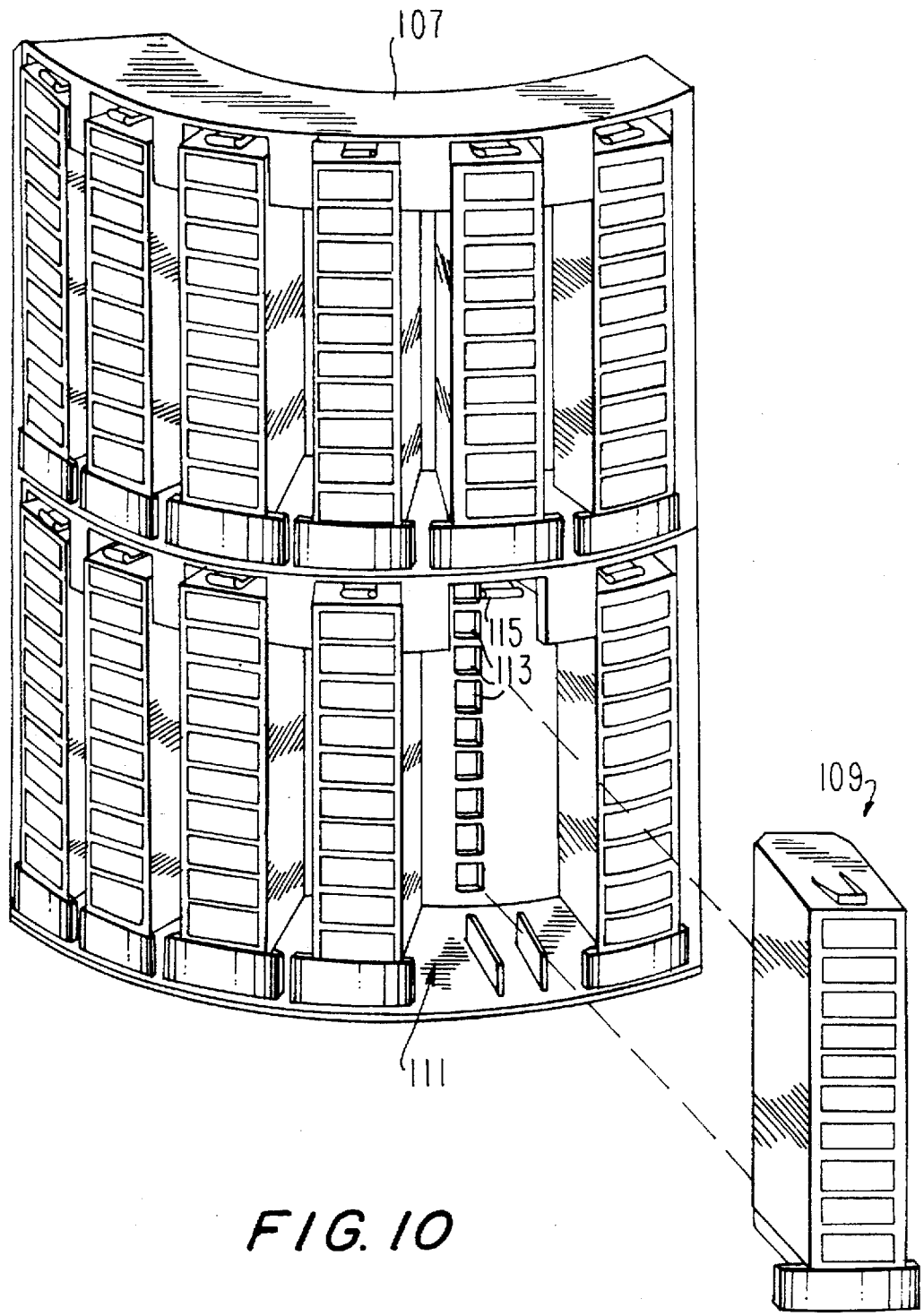
FIG. 10 is a partially exploded perspective view of one of the segments of the assay module supply apparatus shown in FIG. 1 with a plurality of magazines mounted therein.

As can be seen in greater detail in FIG. 10, each segment 107 has a plurality of generally rectangularly shaped chambers 111 circumferentially spaced thereon in two sections. The back wall of each chamber 111 includes a plurality of vertically spaced openings 113 the purpose of which will become apparent below. A downwardly-biasing tab 115 extends into each chamber 11, tab 115 being used to removably secure magazine 109 within chamber 111 in snap-lock fashion.

Figure 11:
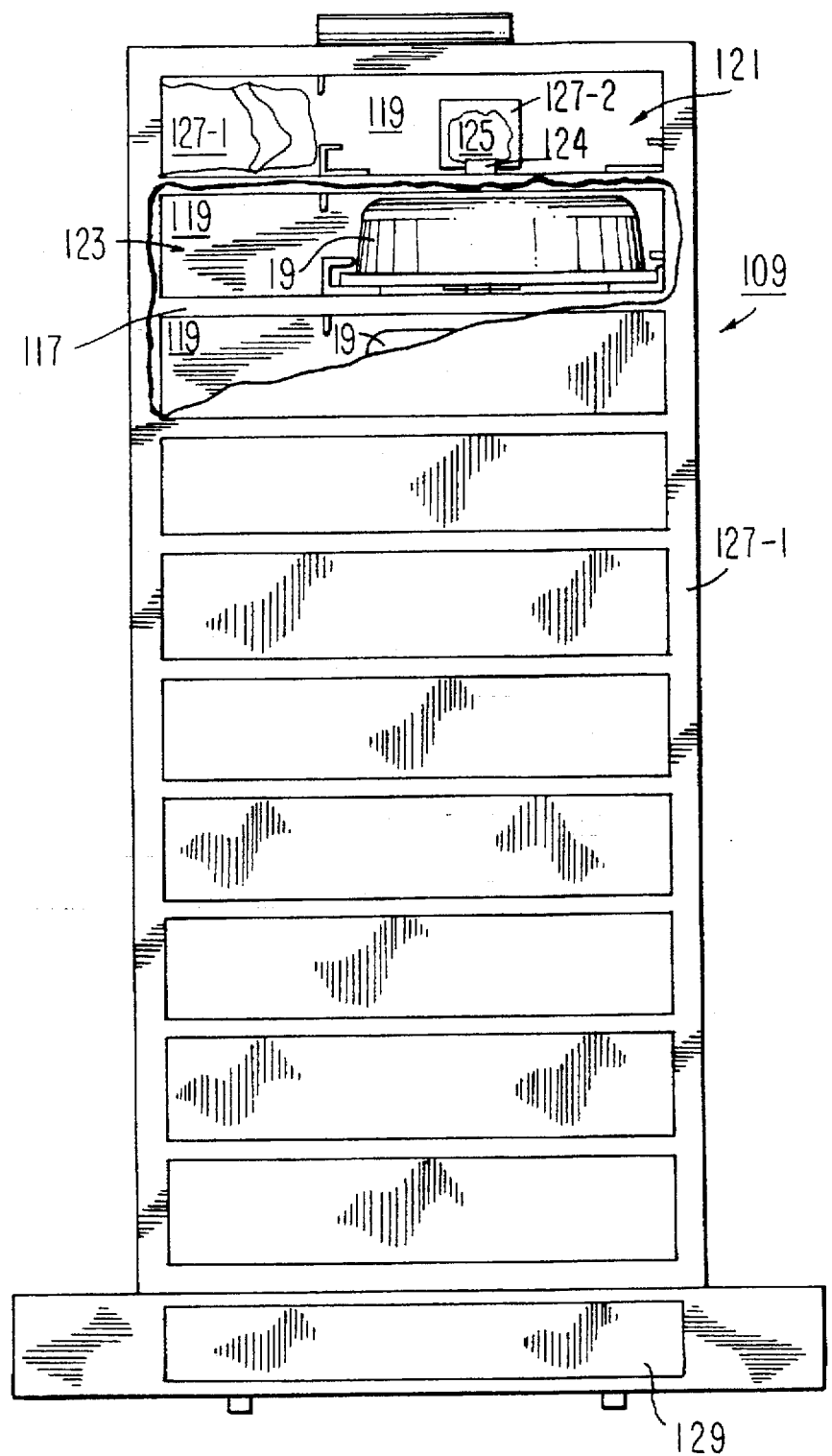
FIG. 11 is an enlarged front view, broken away in part, of one of the magazines shown in FIG. 10.
Figure 12:
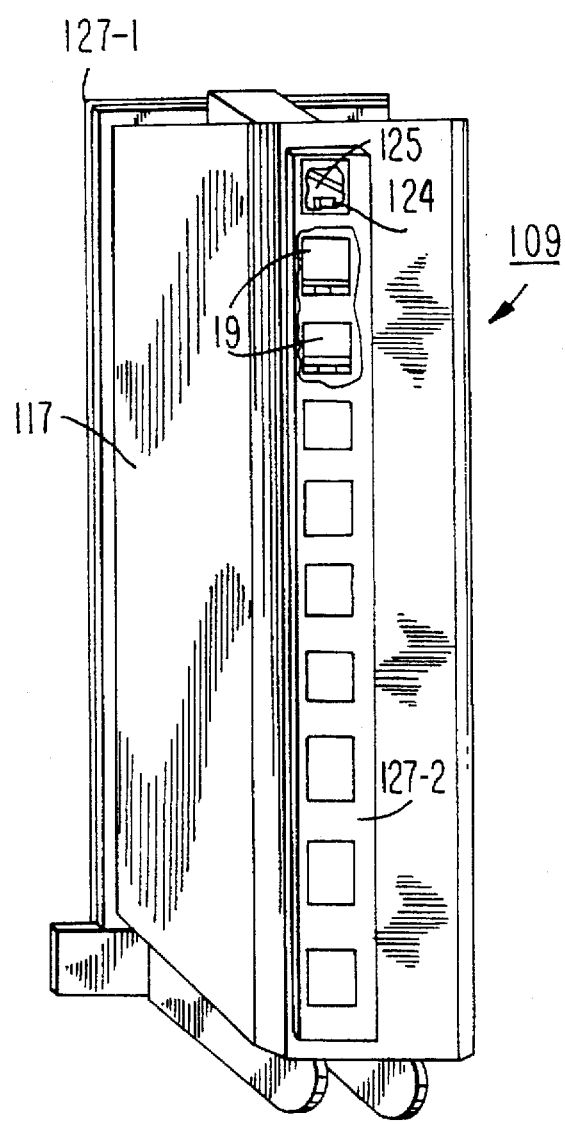
FIG. 12 is a rear perspective view, broken away in part, of the magazine shown in FIG. 11.

A single magazine 109 is shown in greater detail in FIGS. 11 and 12 (one assay module 19 having been removed from magazine 109 in the manner to be described below, magazine 109 being broken away in part to reveal two additional assay modules 19 contained therewithin). As can be seen, magazine 109 comprises a generally rectangularly-shaped, open-faced vessel 117. Vessel 117 is internally sectioned so as to define a plurality of vertically stacked compartments 119, each compartment being further subdivided into a pair of horizontally adjacent sections 121 and 123, respectively, section 121 being used to hold a single assay module 19 (preferably seated therewithin in a nose-in orientation) and section 123 being used to receive a piece of the material covering compartment 119 once it has been cut away therefrom in the manner described below. An upwardly biasing tab 124 is formed at the rear end of section 121 of each compartment 119. Tab 124, which is adapted to engage the bottom of an assay module 19, is used to restrict longitudinal movement of the assay module within section 121 of compartment 119 until the appropriate time for its ejection therefrom. An opening 125 is formed in the back wall of each compartment 119 of vessel 117 to permit access to the nose end of the assay module seated therewithin for reasons to be discussed below. When magazine 109 is mounted within segment 107, openings 125 of vessel 117 become aligned with openings 113 of segment 107.

Sheets of material 127-1 and 127-2, which may be a thin foil or other like material for preventing moisture or debris from entering compartments 119 are adhered to the front and rear surfaces, respectively, of vessel 117. A label 129 having imprinted thereon a bar code or other similar information readable by a bar code reader or the like is affixed to the bottom of vessel 117 for purposes of identifying the specificity of the assay modules contained within vessel 117.

Figure 13:
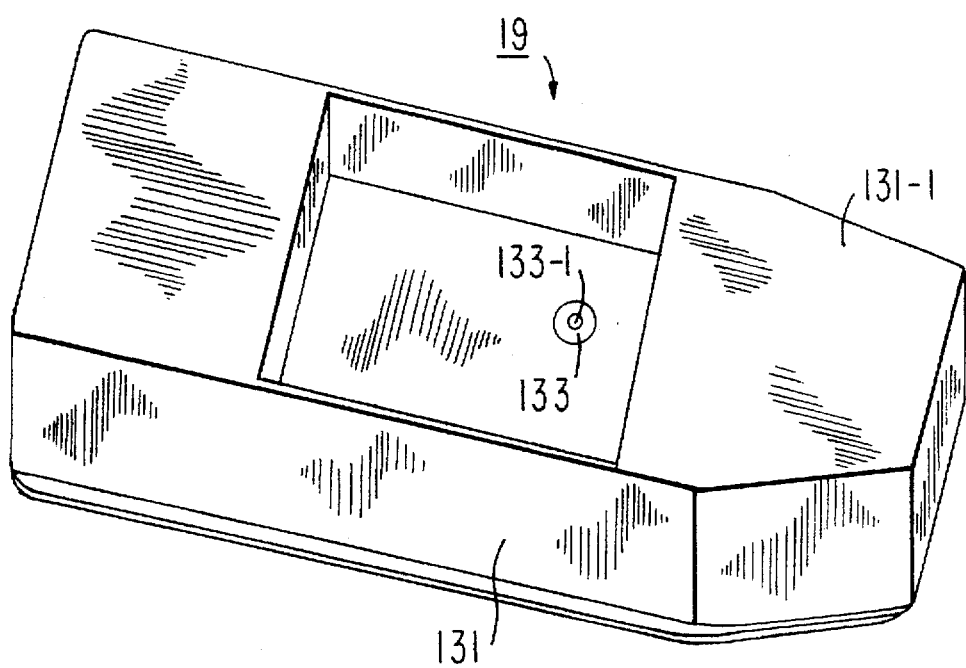
FIG. 13 is an enlarged perspective view of one of the assay modules shown in FIG. 11.

Referring now to FIG. 13, an assay module 19 is shown in greater detail. As can be seen, assay module 19 is an elongated boat-shaped structure 131 having an inwardly tapering nose 131-1. An opening 133 is provided inside assay module 19 to provide access to a reagent bearing film 133-1 contained therein.

Referring back to FIG. 9, assay module transport assembly 23 can be seen to include a scaffolding 141. Scaffolding 141 includes a first pair of legs 143-1 and 143-2 which extend downwardly through the inside of frame 101 and are attached at their bottom ends to a fixed plate 145 concentrically disposed within turntable 24. Plate 145 is coupled to the turntable 103 through a bearing to allow the turntable to rotate while plate 45 remains fixes. Scaffolding 141 also includes a second pair of legs 147-1 and 147-2 which extend downwardly in front of assay module supply apparatus 13 and are attached at their bottom ends to frame 36.

Assay module transport assembly 23 also includes an assay module ejector mechanism 151, which is used to eject a desired assay module 19 from assay module supply apparatus 17 in the manner to be described below. In order that is vertical positioning may be adjusted to access assay modules 19 at various vertical levels within supply apparatus 17, ejector mechanism 151 is mounted on a plate 152, which in turn is mounted on a lead screw 153. Lead screw 153 is coupled to a stepper motor 155 by a belt 157. The operation and direction of motor 155 are controlled by the microprocessor. As a result of this elevator-type arrangement, lead screw 153 draws plate 152 and, hence, ejector mechanism 151 either up or down depending on the direction in which lead screw 153 is turned by motor 155. A guide post 159 is additionally provided to prevent plate 152 from rotating due to the turning movement of lead screw 153.

Assay module transport assembly 23 additionally includes an assay module receiving platform 161, which is sued to receive an assay module 19 which has been ejected from assay module supply apparatus 17 by assay module ejector mechanism 151. Assay module receiving platform 161 is mounted on a second elevator-type arrangement comprising a plate 162, a lead screw 163 on which plate 162 is mounted and a stepper motor 165 to which lead screw 163 is coupled by a belt 167. The operation and direction of motor 165 is also controlled by the microprocessor. A guide post 169 is additionally provided to prevent plate 162 form rotating as lead screw 163 is turned.

Assay module transport assembly 23 further includes a cutter assembly 171 which, as will be seen below, is used to tear away that portion of sheet of material 127-1 covering a desired compartment 119 of magazine 109 and then to tuck the torn strip of material into section 123 of compartment 119. Cutter assembly 171 is fixedly mounted on the bottom of plate 162.

Assay module transport assembly 23 also includes an assay module transfer apparatus 173 which, as will be seen below, serves to move an assay module 19 from assay module receiving platform 161 to an assay module berth 175 formed on turntable 24.

In addition to assay module supply apparatus 17, assay module transport assembly 23, and turntable 24, a PC board 177 is also shown in FIG. 9. Board 177, which is connected to the microprocessor, includes a pair of bar code readers 179 for reading the bar codes printed on labels 129, the pair of bar code readers 179 being positioned so that one bar code reader 179 reads the bar codes located on the top row of magazines 109 in segment 107 and the other bar code reader 179 reads the bar codes located on the bottom row of magazines 109 in segment 107. Board 177 also includes a plurality of assay module detectors 181, each detector 181 comprising an LED (not shown) whose output is directed at a specific compartment 119 of magazine 109 and a light detector (not shown) positioned to detect light reflected off the piece of material 127-1 covering the particular compartment. If the piece of material covering a compartment has not been removed, light emitted by the LED will be reflected off the piece of material and detected by the light detector, indicating that an assay module is present within the compartment. If, however, the piece of material has been removed, then the light emitted by the LED will not be reflected off the piece of material covering the compartment and will not be detected by the light detector, indicating that an assay module is not present within the compartment.

Figure 14:
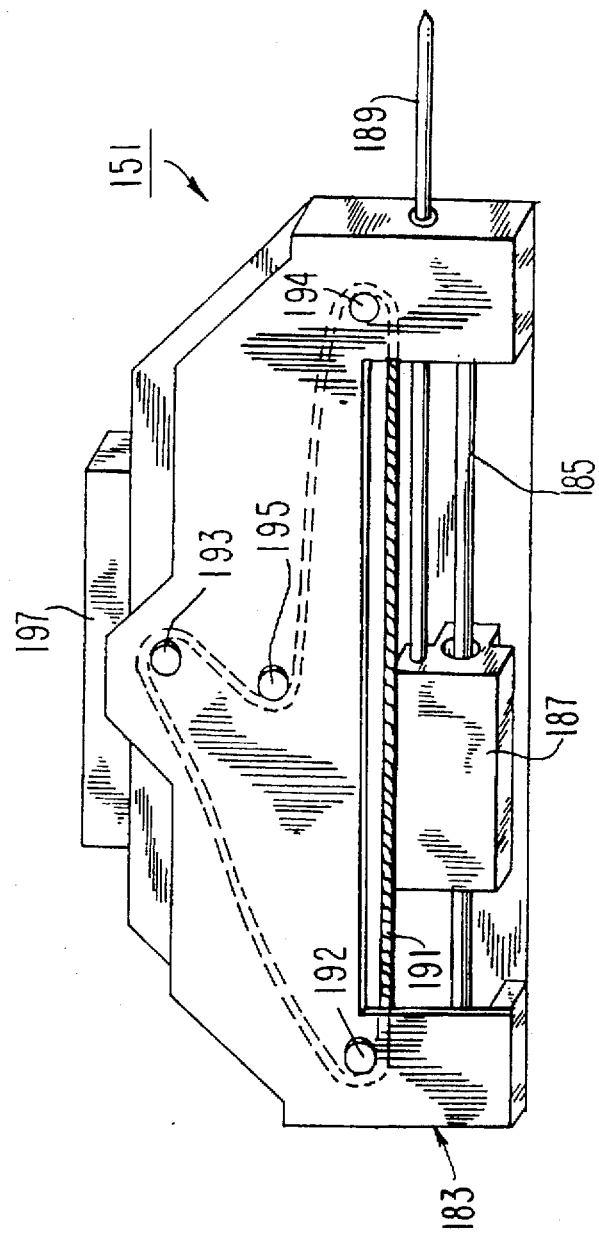
FIG. 14 is an enlarged front perspective view of the assay module ejector mechanism shown in FIG. 9.

Referring now to FIG. 14, there is shown an enlarged front perspective view of assay module ejector mechanism 151. As can be seen, assay module ejector mechanism 151 includes an elongated supporting bracket 183, which is adapted to be mounted on plate 152 (see FIG. 9). A supporting rod 185 extends along the length of bracket 183 and is mounted at the opposite ends thereof. A slider block 187 is mounted on rod 185 for forward and rearward longitudinal sliding movement thereon. A pusher rod 189 which, as will be seen below, is used to pierce layer of material 127-2 and push an assay module 19 form magazine 109 onto assay module receiving platform 161, is mounted on the leading end of slider block 187. Slider block 187 is fixedly attached by any suitable means, not shown, to an endless belt 191 which is mounted for movement along a path defined by wheels 192, 193, 194, and 195. Belt 191 is driven by a stepper motor 197 whose output shaft is fixedly attached to wheel 195. The operation and direction of stepper motor 197 is controlled by the microprocessor.

Figure 15:
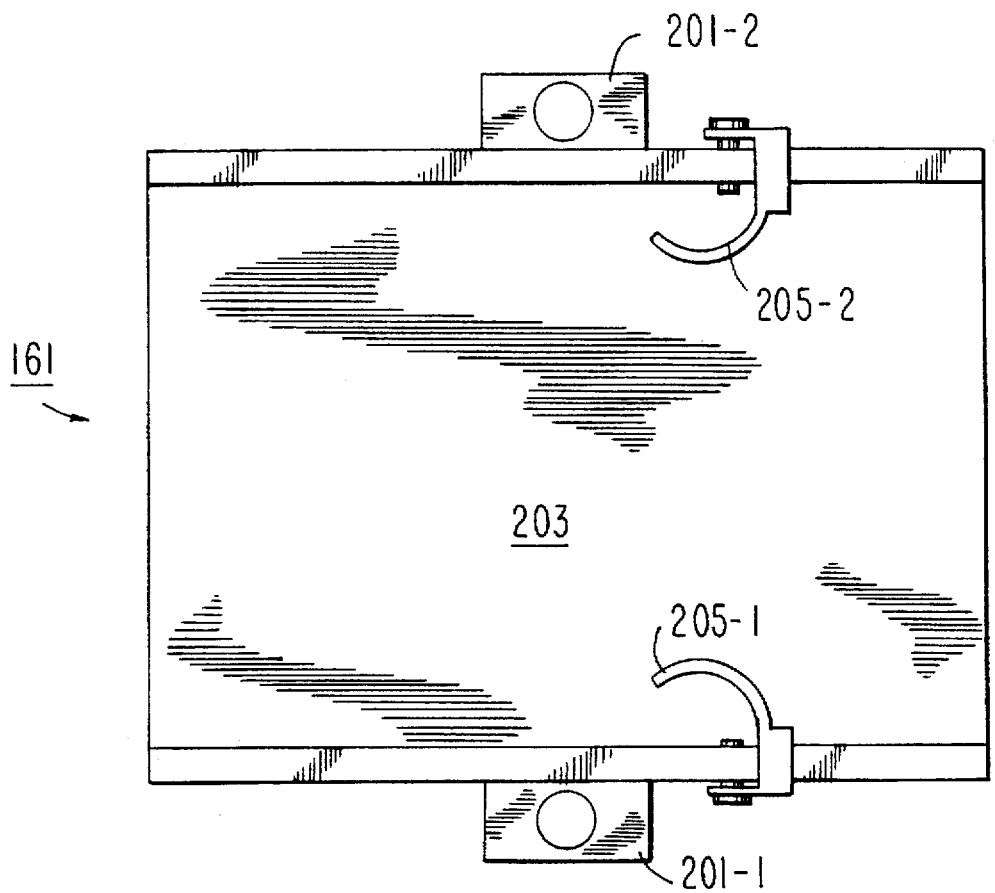
FIG. 15 is an enlarged top view of the assay module receiving platform shown in FIG. 9.

Referring now to FIG. 15, there is shown an enlarged top view of assay module receiving platform 161. As can be seen, assay module receiving platform 161 includes a pair of outwardly extending flanges 201-1 and 201-2 adapted to receive a screw or the like for securing platform 161 to plate 162 (see FIG. 9) and a generally rectangularly shaped trough 203 dimensioned to correspond generally to the size and shape of an assay module 19. A pair of inwardly biasing clips 205-1 and 205-2 are mounted on trough 203 to provide a small amount of resistance so that an assay module 19 will not be pushed too far across trough 203 as a result of the force imparted to the assay module 19 by pusher rod 189 of ejector mechanism 151.

Figure 16:
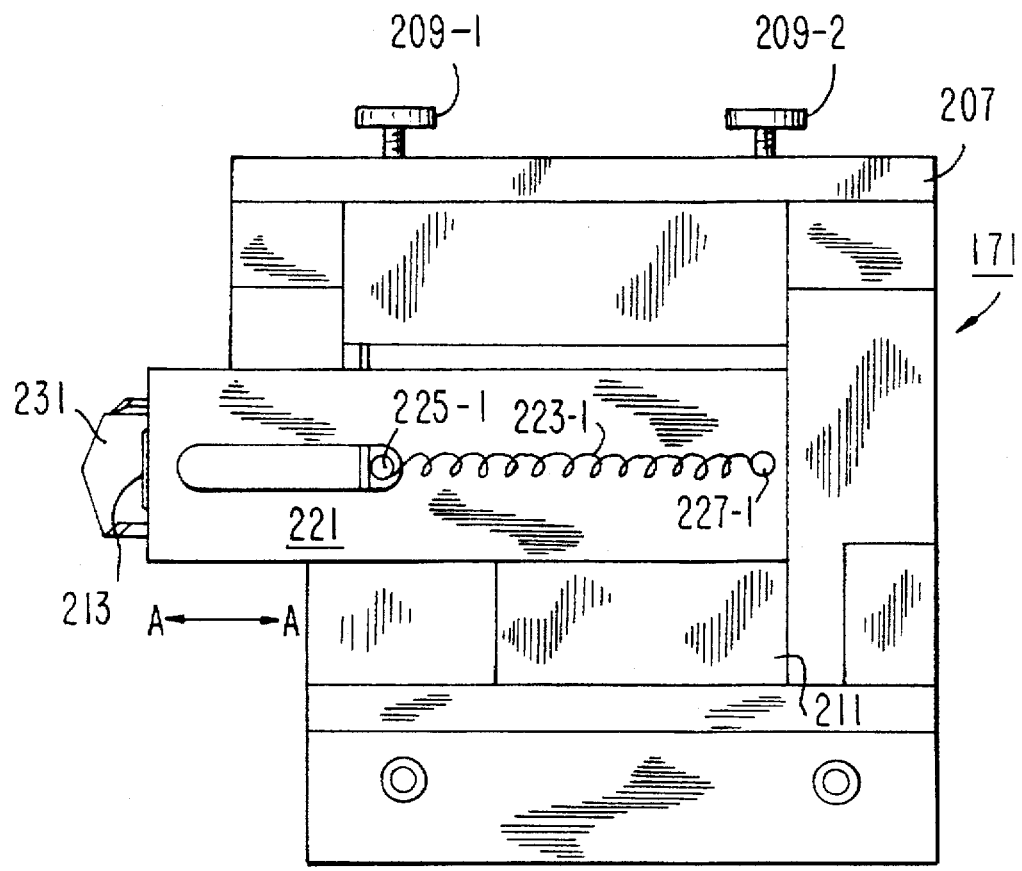
FIG. 16 is an enlarged front view of the cutter assembly shown in FIG. 9.
Figure 17:
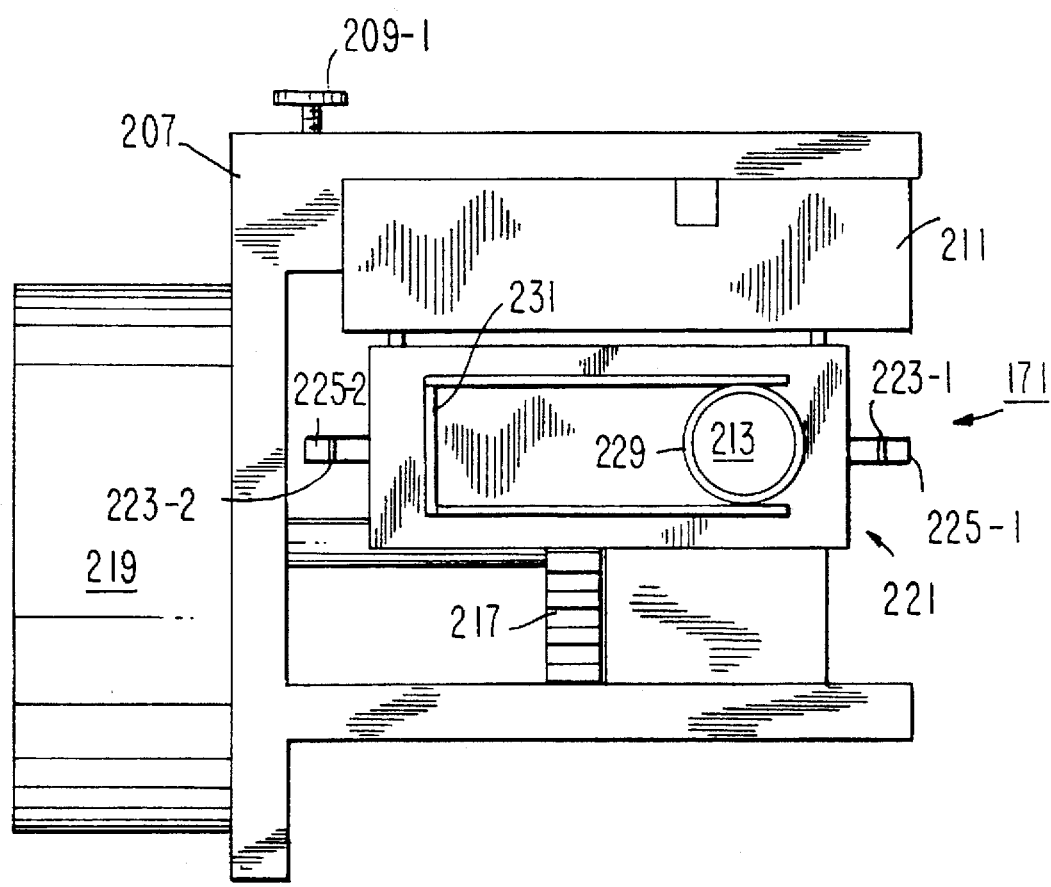
FIG. 17 is a left side view of the cutter assembly shown in FIG. 16.
Figure 18:
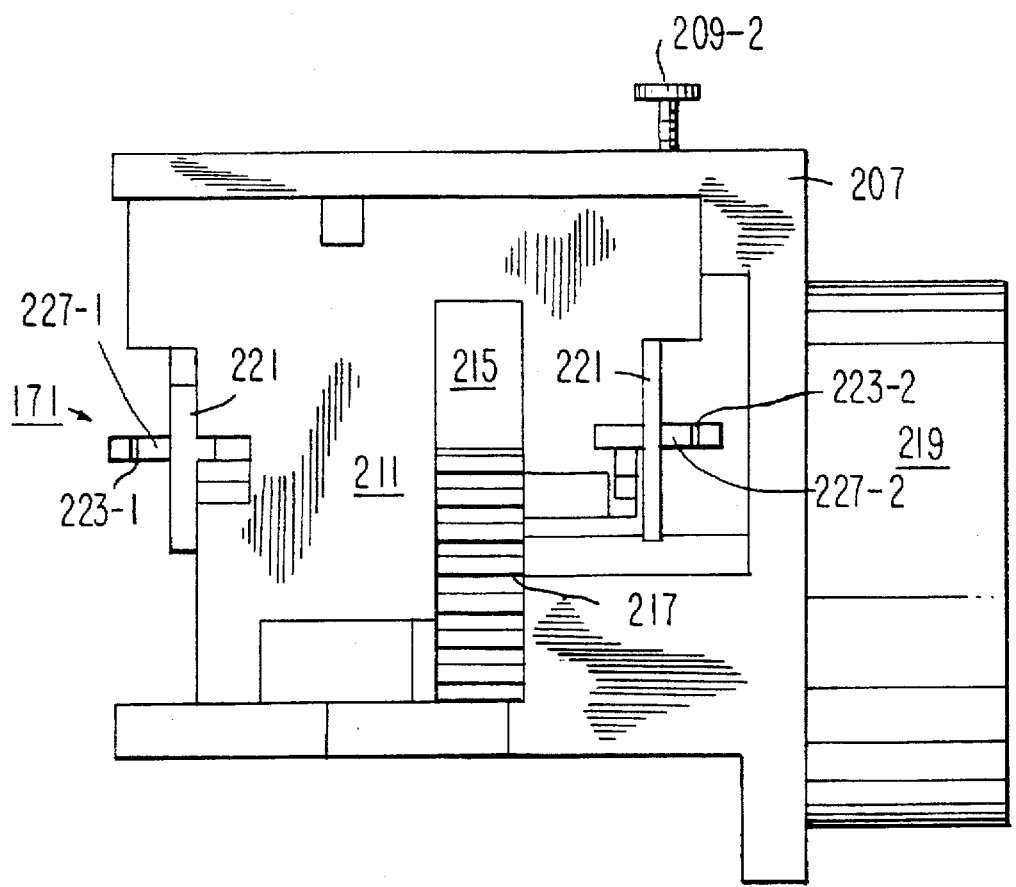
FIG. 18 is a right side view of the cutter assembly shown in FIG. 16.

Referring now to FIGS. 16 through 18, there are shown various views of cutter assembly 171. As can be seen, cutter assembly 171 includes a generally C-shaped supporting bracket 207, which is adapted to be mounted on the bottom of plate 162 (see FIG. 9) with a pair of screws 209-1 and 209-2. A block 211 is slidably mounted inside bracket 207. One end of block 211 is shaped to define a cylindrically-shaped, finger-like projection or plunger 213. As will be seen below, plunger 213 is used to tuck the piece of material from layer 127-1 which has been cut in the manner hereinafter described into section 123 of compartment 119. A rack 215, which is engaged by a pinion 217 driven by a stepper motor 219, is mounted along block 211, the rack and pinion arrangement permitting block 211 to be moved back and forth across bracket 207 in either of the directions indicated by arrows A in FIG. 16 according to instructions given to motor 219 by the microprocessor.

Cutter assembly 171 also includes a generally C-shaped cutter element 221. Cutter element 221 is slidably mounted on block 211 but is biased towards plunger 213 by a pair of springs 223-1 and 223-2, which are mounted at one end on a pair of posts 225-1 and 225-2, respectively, fixedly attached to block 211 and at their opposite ends on a pair of posts 227-1 and 227-2, respectively, fixedly attached to the sides of cutter element 221. The transverse portion of cutter element 221 includes an opening 229 through which plunger 213 of block 211 extends when element 221 is moved relative to block 211 in the manner discussed below. The transverse portion of cutter element 221 also includes a blade element 231 which, as will hereinafter be discussed, is used to cut that portion of material layer 127-1 covering three sides, for example, the top, bottom, and right side edges of compartment 119.

Figure 19:
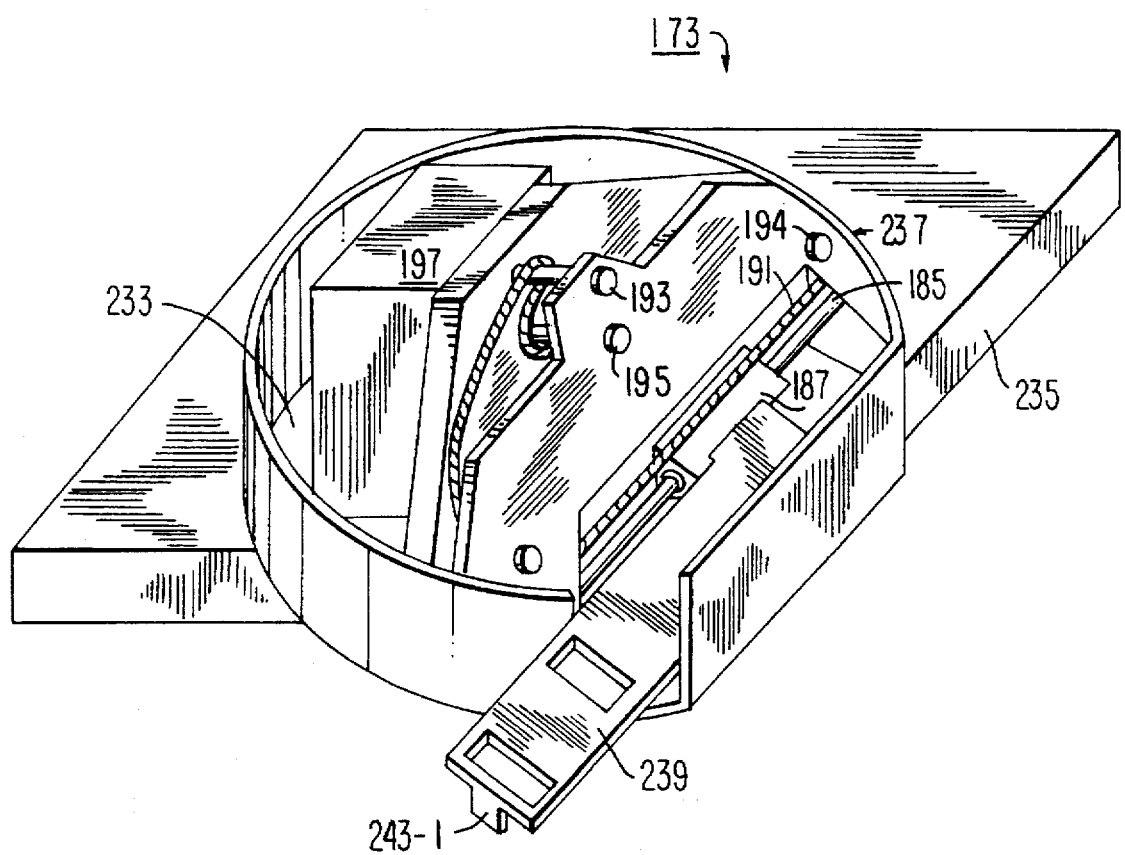
FIG. 19 is an enlarged perspective view of the assay module transfer mechanism shown in FIG. 9.
Figure 20:
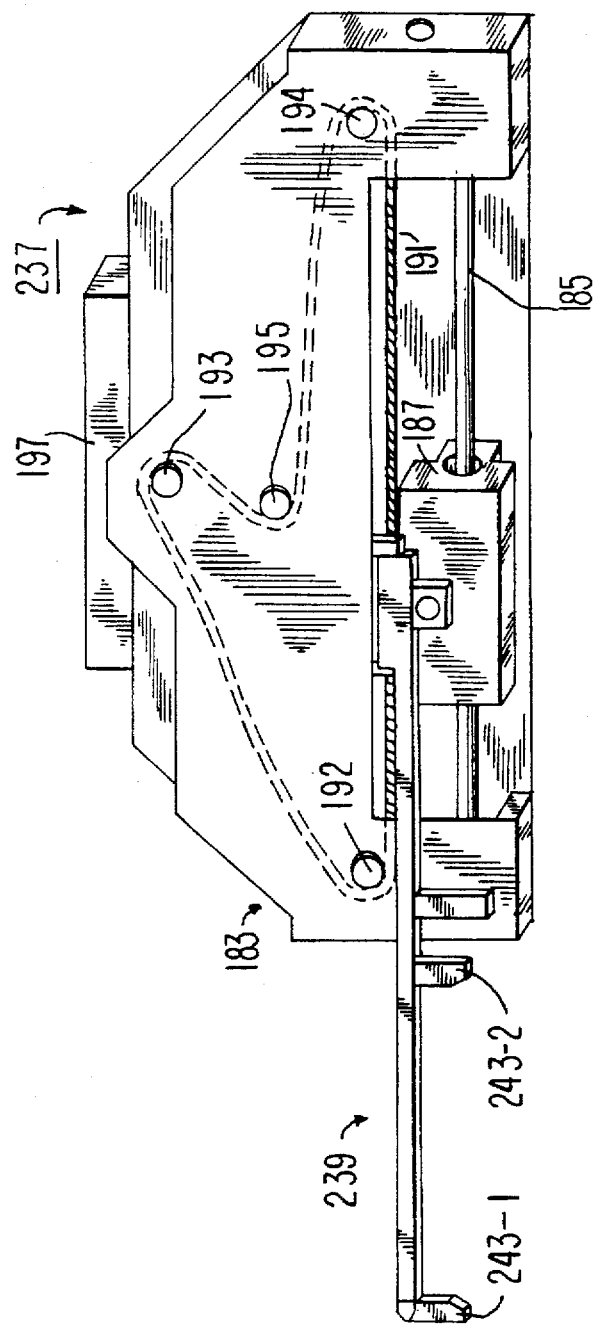
FIG. 20 is a perspective view of the assay module loader assembly shown in FIG. 19.

Referring now to FIG. 19, there is shown an enlarged perspective view of assay module transfer mechanism 173. As can be seen, assay module transfer mechanism 173 includes a platform 233. Platform 233 is rotatably mounted on a shaft (not shown) which is coupled through a belt (not shown) to a stepper motor 235. The operation and direction of stepper motor 235 are controlled by the microprocessor. Mounted on top of platform 233 is an assay module loader assembly 237. As can be seen in FIG. 20, assay module loader assembly 237 is virtually identical in construction to assay module ejector mechanism 151, the only difference between assay module loader assembly 237 and assay module ejector mechanism 151 being that assay module loader assembly 237 does not have a pusher rod 189 mounted on the leading end of slider block 187, but rather, has a loader arm 239, which is fixedly mounted with a screw 241 or similar means on the font side of slider block 187. Loader arm 239, which is shown in isolation in FIG. 21, has a pair of downwardly-extending tabs 243-1 and 243-2 which are adapted to engage the nose and rear ends, respectively, of assay module 19 in the manner to be described below so that assay module 19 may be pulled off assay module receiving platform 161 and then pushed onto an assay module berth 175 on turntable 24.

When assay module transport assembly 23 is not in use, assay module transfer mechanism 173 is positioned so that platform 233 is rotated towards chamber 21 and loader arm 239 is fully extended over turntable 24. When actuation of assay module transport assembly 23 is desired, turntable 24 is rotated until a sued and no longer needed assay module seated on turntable 24 comes into engagement with loader arm 239. Loader arm 239 then retracts, pulling the used assay module onto platform 233 and leaving an empty assay module berth 175 on turntable 24. Next, platform 233 makes an approximately quarter-turn rotation after which loader arm 239 extends again, ejecting the used assay module from platform 233 into a sued assay module receptacle (not shown). Loader arm 239 then retracts again and platform 233 rotates until loader arm 239 is aligned with assay module receiving platform 161.

Either at the same time, before, or after the above-recited sequence of events, turntable 103 rotates, if necessary, so that the magazine 109 containing the assay module which it is desired to remove therefrom becomes rotationally aligned with cutter assembly 171. Plate 162 is moved vertically, if necessary, so that cutter assembly 171 is aligned vertically with the compartment 119 containing the desired assay module. Next, the rack and pinion arrangement of cutter assembly 171 drives block 211 (and, hence, cutter element 221) horizontally towards the compartment 119 containing the desired assay module. This horizontal movement causes blade element 231 of cutter element 221 to server three sides, for example, the top, bottom, and right side edges of that portion of the layer of material 127-1 covering compartment 119; however, further horizontal movement of cutter element 221 towards compartment 119 is restrained as the remaining surface of the transverse portion of cutter element 221 comes into contact with that portion of vessel 117 surrounding the compartment 119. Despite the stoppage of movement of cutting element 221, block 211 continues to move horizontally in the direction of compartment 119, causing plunger 213 to extend through opening 229 of cutting element 221 in such a way as to push the now torn piece of the layer of material 127-2 into section 123 of compartment 119. The rack and pinion arrangement then reverses direction causing block 211 and cutting element 221 to retract.

Plate 162 then moves downwardly so that assay module receiving platform 161 is aligned vertically with the compartment 119 containing the desired assay module. Either at the same time, before, or after the above-recited sequence of events, plate 152 is moved vertically, if necessary, so that pusher rod 189 of assay module ejector mechanism 151 is vertically aligned with the compartment 119 containing the desired assay module. Pusher rod 189 is then moved horizontally towards the desired compartment 119 whereby it passes through the opening 113 on the back of the segment 107, pierces that portion of layer of material 127-2 covering opening 125 of the desired compartment 119, passes through opening 125, and pushes the nose end 131-1 of the desired assay module 19 out of compartment 119 and onto platform 161. Pusher rod 189 is then retracted.

With the desired assay module now on assay module receiving platform 161, plate 162 then moves vertically, if necessary, to a waiting position just below the plane of loader arm 239. Loader arm 239 is then extended, and plate 162 moves vertically upwardly until the assay module on platform 161 engages tabs 243-1 and 243-2 of loader arm 239. Loader arm 239 then retracts, pulling the assay module off platform 161 and onto platform 233. Platform 233 then rotates so that loader arm 239 is aligned with the empty assay module berth 175 on turntable 24, and loader arm 239 is extended so that the desired assay module is inserted into the empty berth 175. Turntable 24 then rotates so that the new assay module is no longer aligned with loader arm 239. Loader arm 239 is then ready to receive another used assay module disposed on turntable 24 and the above-described sequence of events may be repeated.

The embodiments of the present invention are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. An automated analytical instrument for use in conducting assays for a component of interest in a fluid sample, said automated analytical instrument comprising:

a. an assay module supply unit for holding a supply of assay modules;

b. a testing system for assaying the fluid sample for a component of interest using an assay module; said testing system including a fluid dispensing assembly;

c. an assay module transport assembly for transporting the assay module form said assay module supply unit to said testing system;

d. a fluid sample holding tray transport assembly for transporting a fluid sample holding tray carrying fluid sample holding containers wherein said fluid sample holding tray transport assembly includes:

i. a conveyor for transporting the fluid sample holding tray along a path past said fluid dispensing assembly whereat quantities of sample fluids can be aspirated from said fluid sample holding containers and for transporting the fluid sample holding tray away form said fluid dispensing assembly, wherein said conveyor includes carriage means for receiving the fluid sample holding tray;

ii. a fluid sample holding tray loading unit for loading a fluid sample holding tray onto said conveyor for transport to said fluid dispensing assembly, said loading unit adapted to hold a plurality of fluid sample holding trays hereon and including means for detected the presence of a fluid sample holding tray hereon;

iii. a fluid sample holding tray unloading unit for unloading a fluid sample holding tray from said conveyor at a location past said fluid dispensing assembly said unloading unit adapted to hold a plurality of fluid sample holding trays thereon;

iv. whereby said conveyor for transporting the fluid sample holding tray by a reversibly driven stepper motor controlled by a microprocessor to load, move, dispense and unload a rush fluid sample holding tray from a row of fluid sample loading trays on the loading unit for processing and return said rush tray to the unloading unit for disposal, and continue to automatically select the next fluid sample tray form the unloading unit and conveying it back along the fluid sample holding tray transport assembly path.

* * * * *